United States Patent
Adam (10) Patent No.: US 9,417,122 B2
(45) Date of Patent: Aug. 16, 2016

(54) SELF-CLEANING LENS

(75) Inventor: Quentin Arthur Carl Adam, Sydney (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 38 days.

(21) Appl. No.: 13/879,800

(22) PCT Filed: Jun. 15, 2012

(86) PCT No.: PCT/US2012/042626
§ 371 (c)(1),
(2), (4) Date: Apr. 16, 2013

(87) PCT Pub. No.: WO2013/187910
PCT Pub. Date: Dec. 19, 2013

(65) Prior Publication Data
US 2013/0334111 A1 Dec. 19, 2013

(51) Int. Cl.
*G01J 1/04* (2006.01)
*G02B 27/00* (2006.01)
*A61B 1/00* (2006.01)
*G01N 21/15* (2006.01)
*G01J 1/02* (2006.01)

(52) U.S. Cl.
CPC ........... *G01J 1/0411* (2013.01); *A61B 1/00057* (2013.01); *G01J 1/0252* (2013.01); *G01N 21/15* (2013.01); *G02B 27/0006* (2013.01)

(58) Field of Classification Search
None
See application file for complete search history.

(56) References Cited

U.S. PATENT DOCUMENTS

| | | | | |
|---|---|---|---|---|
| 3,867,837 | A * | 2/1975 | Malin | 73/73 |
| 5,039,492 | A * | 8/1991 | Saaski et al. | 422/82.09 |
| 5,489,536 | A * | 2/1996 | Ekechukwu | 436/169 |
| 6,326,228 | B1 * | 12/2001 | Hughes et al. | 438/49 |
| 7,858,035 | B2 | 12/2010 | Cronin et al. | |
| 8,399,839 | B2 * | 3/2013 | Huttmann et al. | 250/343 |
| 8,718,738 | B2 * | 5/2014 | Blank et al. | 600/344 |
| 2001/0039033 | A1 | 11/2001 | Ogawa | |
| 2005/0183968 | A1 | 8/2005 | Pendergrass | |
| 2006/0073585 | A1 | 4/2006 | McDevitt et al. | |
| 2007/0068495 | A1 | 3/2007 | Karst | |
| 2010/0087798 | A1 * | 4/2010 | Adams et al. | 604/515 |

FOREIGN PATENT DOCUMENTS

| | | |
|---|---|---|
| CA | 2015524 | 4/1990 |
| JP | 63-221318 | 9/1988 |

OTHER PUBLICATIONS

Borecki et al., "Intelligent Photonic Sensors for Application in Decentralized Wastewater Systems," Waste Water—Evaluation and Management, Apr. 1, 2011, 23 pages.

Dickert et al., "Chemical Sensors—from Molecules, Complex Mixtures to Cells—Supramolecular Imprinting Strategies," Sensors, 2003, pp. 381-392, vol. 3.

(Continued)

*Primary Examiner* — Terry Cecil
(74) *Attorney, Agent, or Firm* — Maschoff Brennan (57) ABSTRACT

Some embodiments herein generally relate to self-clean lenses, sensor systems, and/or methods of cleaning. In some embodiments, a self-cleaning lens is provided for a sensor for monitoring a liquid.

16 Claims, 5 Drawing Sheets

(56) References Cited

OTHER PUBLICATIONS

International Search Report and Written Opinion dated Aug. 13, 2012, received in International Application No. PCT/US2012/042626, filed on Jun. 15, 2012.

Reverse Osmosis (from Wikipedia), information was available at website: http://en.wikipedia.org/wiki/Reverse_osmosis; in some form no later than Jan. 10, 2012. While no copy of the website as it existed on Jan. 10, 2012, is in Applicant's possession, Applicant has provided the website that was printed on Nov. 29, 2012.

* cited by examiner

SELF-CLEANING LENS

CROSS-REFERENCE TO RELATED APPLICATION

This application is the U.S. national phase entry under 35 U.S.C. §371 of PCT/US2012/042626, filed on Jun. 15, 2012, the entire disclosure of which is hereby incorporated by reference herein.

FIELD

Embodiments herein relate generally to devices and systems for cleaning and/or maintaining clean lenses and/or surfaces.

BACKGROUND

Sensors are frequently used in various liquid applications in order to monitor various aspects or characteristics of the liquid. Such sensors, and their application and use, frequently must take into account the ability to observe the liquid, and at the same time, protect the sensor from the liquid. A protective layer between the sensor and the liquid to be observed can offer some degree of protection.

SUMMARY

In some embodiments, a sensor device is provided. The sensor device can include a sensor having a sensing surface, a transparent, fluid-permeable lens positioned in front of the sensor, and a chamber positioned between the sensor and the lens, such that radiation can pass through the lens and into the sensor to the sensing surface.

In some embodiments, a method of cleaning a sensing device is provided. The method can include providing a sensor, providing a fluid-permeable lens, providing a fluid between the sensor and the fluid-permeable lens, and allowing the fluid to pass through the fluid-permeable lens. This creates a fluid boundary on an outer surface of the lens to clean the outer surface of the lens.

In some embodiments, a water-permeable lens is provided. The lens can include a water-permeable membrane that is transparent to at least one wavelength of electromagnetic radiation. The membrane can have a refractive index that is substantially identical to a refractive index of water. The membrane can allow water to passively pass through the lens at a rate of at least 1 liter per day.

In some embodiments, a greywater monitoring system is provided. The system can include an optical sensor, a fluid-permeable lens, a source of cleaning fluid in fluid communication with the fluid-permeable lens, and a greywater channel. The optical sensor is in optical communication with the channel via the fluid-permeable lens.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

While sensors can be useful in monitoring various environments, frequently, these environments can be detrimental to the integrity of the sensing device itself. As such, sensors can be encased and/or located behind a lens so that the sensor can monitor what is occurring through the window or lens, without risking damage to the sensor itself. While the lens can provide protection to the sensor, contaminants from the environment can often build up on the lens, obstructing the sensor, and making the sensors nonfunctional in a different manner. Presented herein are methods and devices for assisting in keeping such lenses clean and/or at least cleaner and/or protected from their environment. In some embodiments, this can be achieved by a lens that is self-cleaning. The lens can be permeable to a fluid such that the fluid can pass from one side to the other, thereby cleaning the lens and/or reducing any buildup on the lens. By putting an adequate amount of a fluid on the same side of the lens as the sensor (which can optionally be protected from the fluid), the fluid can flow through the lens. This flow of fluid can act to continuously clean the lens and/or create a buffer of the fluid on the opposite side of the lens, protecting this surface of the lens from contamination by the environment. These and other embodiments are provided herein.

In some embodiments, a sensor device is provided. The sensor device includes a sensor that has a sensing surface and a transparent, fluid-permeable lens positioned in front of the sensor. A chamber is positioned between the sensor and the lens such that radiation can pass through the transparent, fluid-permeable, lens, into the sensor, and then to the sensing surface.

Figure 1:
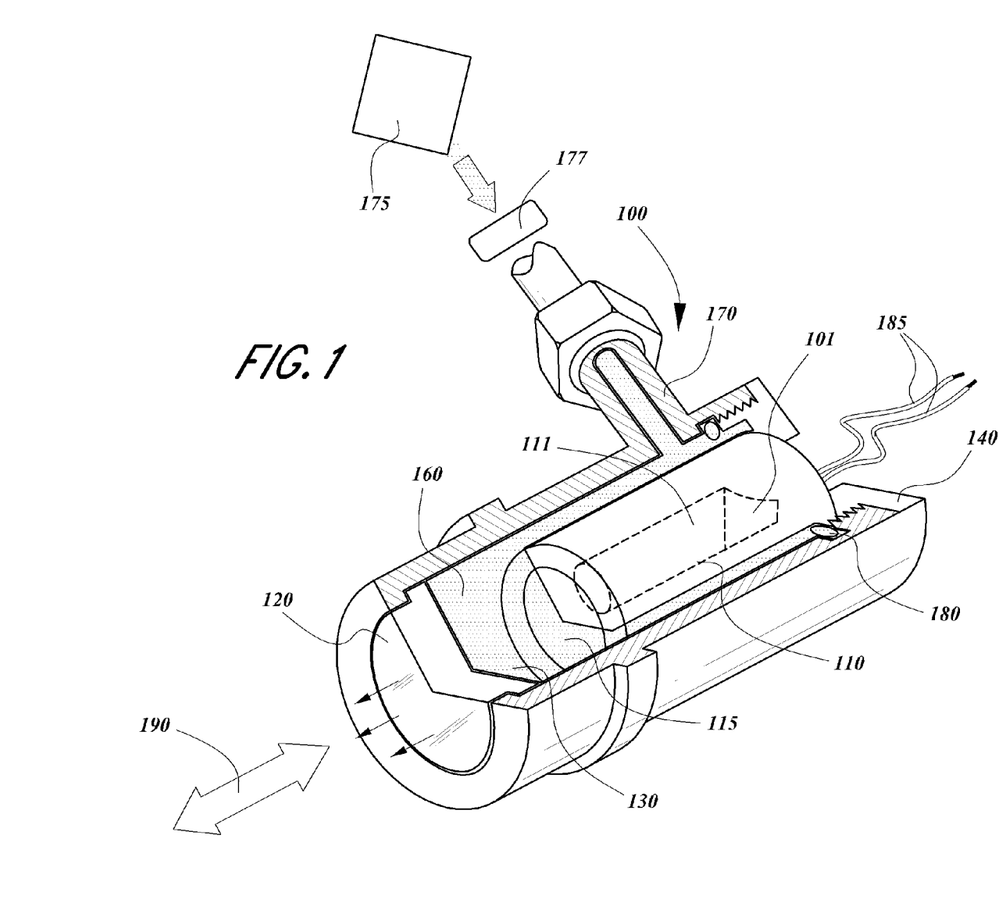
FIG. 1 is a drawing illustrating some embodiments of a sensor device with a self-cleaning lens.

FIG. 1 illustrates some embodiments of a sensor device 100. The sensor device can include a fluid-impermeable casing 110 surrounding a sensor. The sensor device can include a fluid-impermeable surface 115 abutting the sensor. The sensor device can further include a lens 120. The sensor device can further include a chamber 160 positioned between the sensor 111 and the lens (or at least positioned between the lens 120 and a sensing surface 101).

The sensor device can further include an inlet 170, which can optionally be in fluid communication with a source of fluid 175. The fluid can be any type of fluid that will assist in keeping the lens 120 free of build up. The inlet 170 is in fluid communication with the chamber 160. Optionally, a pump 177 can be provided in fluid communication with the inlet and can be configured to move water from the water source 175 into the inlet 170, and subsequently into the chamber 160. The sensor device 100 can further include an optional seal 180 at the first end 140. The seal 180 can include a washer, a gasket, an adhesive, and/or a sealant, thus preventing fluid from exiting the first end 140, for example to prevent fluid from interfering with electronics outside of the first end 140.

The sensor device 100 can further include an optional electrical or optical feed 185 to a processor, thus placing the sensor in data communication with the processor.

Electromagnetic radiation 190 can be transmitted through the environment to be sensed (which can be gas, liquid, etc) and through the lens 120. The electromagnetic radiation 190 can further be transmitted through the chamber 160, and through the fluid impermeable surface 115 abutting the sensor, to reach the sensing surface of the sensor. Not only does the lens 120 allow electromagnetic radiation to pass through it, but, as shown by the arrows in front of the lens, it allows the fluid 130 to pass from the chamber 160 into the environment. In some embodiments, the presence of the fluid 130 is enough to keep the surface of the lens 120 cleaner of environmental contaminants. In some embodiments, as discuss below, the fluid can be supplied in sufficient amounts and/or pressure so that a buffer of the fluid is built up on the outer surface of the lens 120 (where the arrows are), which can serve as a physical barrier from the environment as well.

In some embodiments, the casing 110 can be positioned at or near a first end 140 of the sensor device. The lens can be positioned at either the second end 150 of the sensor device 100, or alternatively between the second end 150 and the casing 110. In some embodiments, the casing 110 can be positioned between the first end 140 and the lens 120, with the lens positioned at or near a second end 150 of the sensor device.

Figure 2:
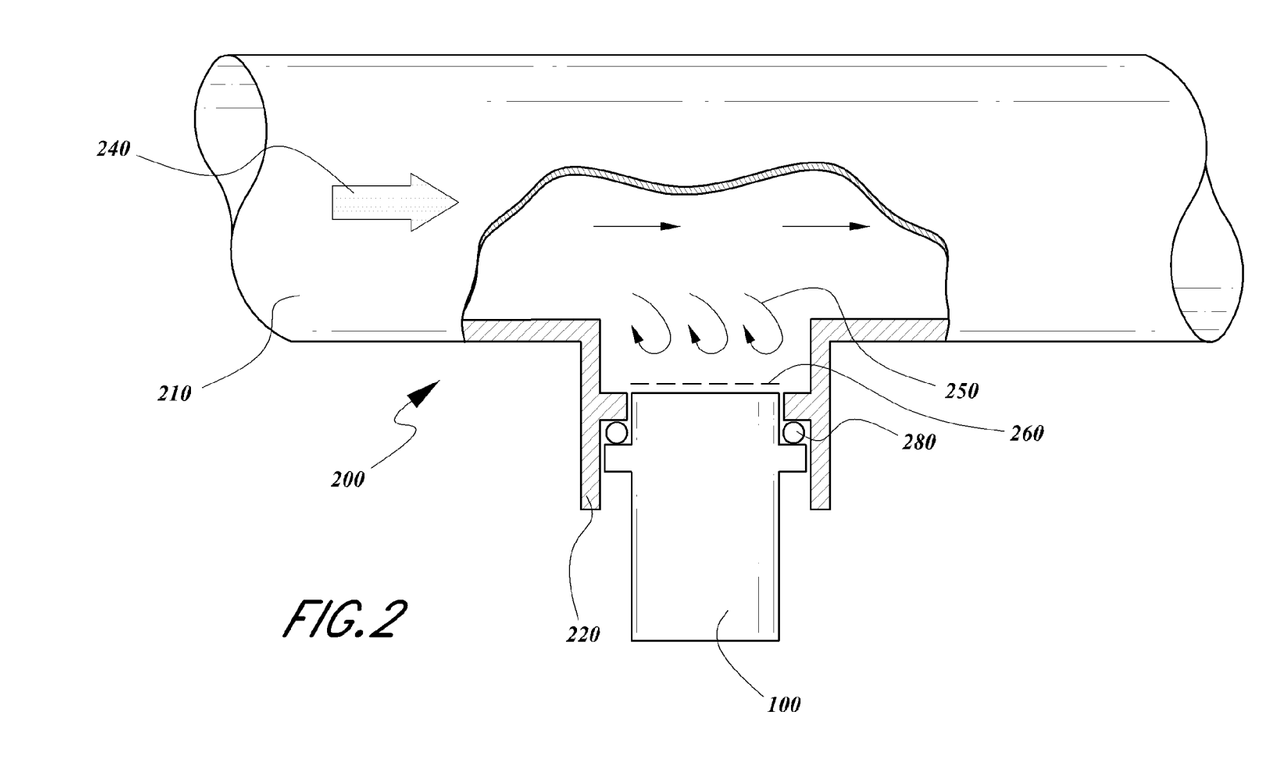
FIG. 2 is a drawing illustrating some embodiments of a self-cleaning lens installed.

FIG. 2 illustrates some embodiments of a sensor device in an installed configuration 200. The installation can include a channel 210 for liquid (or any fluid) to be monitored. The installation can, optionally, include a recessed housing 220 for the sensor device 100. The sensor device 100 can be incorporated via a seal 280 to prevent the leakage of fluid. Liquid to be monitored 240, for example greywater, can flow through the channel 210. Eddies 250 can form at or near the recessed housing. The buffer zone 260 of the fluid 130 can assist in shielding and/or removing any contaminants from the liquid to be monitored 240.

The sensing surface 101 of the sensor 111 can be configured to sense electromagnetic radiation. In some embodiments, any sensor 111 and/or sensing surface 101 that can detect what is desired to be detected in the liquid to be monitored can be used. The sensor and/or sensing surface can be a CCD device, a photomultiplier tube, or any other system for detecting and/or amplifying electromagnetic radiation. In some embodiments, the sensor includes an optical sensor. In some embodiments, the sensor includes a laparoscopic sensor and/or a transducer. In some embodiments, the sensor can be based upon sound waves or other detection devices.

In some embodiments, the sensor 111 includes a casing 110 that is substantially impermeable to fluid. The sensor can be substantially impermeable to fluid. In some embodiments, the sensing surface itself is inert to the fluid 130, and thus, no casing or additional sensor parts are required.

The sensor device 100 includes a lens 120 that is permeable to a fluid. The lens can be transparent to at least one wavelength of electromagnetic radiation. In some embodiments, the lens is transparent to two or more wavelengths of electromagnetic radiation. In some embodiments, the lens is at least about 1% transparent to a wavelength of electromagnetic radiation. In some embodiments, the lens is at least about 90% transparent to a wavelength of electromagnetic radiation.

In some embodiments, the refractive index of the lens 120 is similar to that of the liquid to be monitored. The refractive index of the lens can be similar to that of water. The refractive index of the lens can be similar to that of the fluid 130. The refractive index is calculated as the ratio of the speed of light travelling in a vacuum to the ratio of the speed of light traveling through the material for which the refractive index is calculated. The refractive index is measured for light having the wavelength of the yellow doublet sodium D-line, which is about 589 nanometers. At 20° C., the refractive index for water is about 1.33. The difference between the refractive index of the lens and the refractive index of water can be less than about 20% of the refractive index of water. If the refractive of the lens is significantly greater than water, then the geometry of the lens can be modified to look like a lens with combinations of concave and convex surfaces.

In some embodiments, the lens includes a single layer of material. In some embodiments, the lens includes two or more layers of material. In some embodiments, the lens includes two or more materials. In some embodiments, the material includes polytetrafluoroethylene (e.g., TEFLON) and the lens is made fluid-permeable by pores in the polytetrafluoroethylene. In some embodiments, the lens includes a single layer of polytetrafluoroethylene. In some embodiments, the lens includes two or more layers of polytetrafluoroethylene that have been combined. Adjoining layers can be annealed to each other. In other embodiments, the lens includes foamed polytetrafluoroethylene. Foamed polytetrafluoroethylene can include pores and thus be water (or other fluid) permeable. In some embodiments, the lens includes woven polytetrafluoroethylene threads, for which the weave includes openings or pores as discussed herein. In other embodiments, the lens includes another permeable polymer, for example transparent silicone, nylon, or plastics, such as Cytop.

In some embodiments, the lens includes pores, which can include holes, slots, channels, etc., which allow a fluid to pass from one side of the lens to the other. When a multilayer lens is employed, each layer of the lens can contain pores. In some embodiments, the pores can have diameters that are substantially the same. The pores can be of different sizes, and thus include pores having diameters of two or more sizes. In some embodiments, in order to reduce the accumulation of debris in the chamber 160, the largest pore or pores are larger than the largest particle that typically is found in fluid within the chamber, so that particulates that might make it into the chamber can flow out again. In some embodiments, in order to reduce the accumulation of debris in the chamber 160, the largest pore or pores are smaller than the average and/or smaller sized particle that is found in the liquid to be monitored 240, so as to further reduce the chance that contaminants can accumulate. In some embodiments, the diameter of a pore can be less than about 200 μm. In some embodiments, any sized pore can be used and can depend on the water quality and the filter used upstream of the device.

While the term "lens" is used, the term does not require that the apparatus focus or alter and/or manipulate light in any particular manner (unless specifically noted). Thus, in some embodiments, the term lens will encompass any general barrier and/or window that allows electromagnetic radiation, or other signal information (for example sound waves) to pass through to the relevant sensor and/or sensing surface.

In some embodiments, the pores are perforations in each layer. In some embodiments, the pores are holes bored or drilled through the lens after the layers are assembled, for example holes drilled via a laser drill. In some embodiments, the pores can be gaps between woven fibers of polymer, the size of which is determined by the spacing of the weft and/or the warp of the weave. The pores between the layers do not necessarily have to be aligned on top of each other. Liquid can pass through one pore, then between two layers, then out another pore (for example, for lenses made up from layers of plastic film).

In some embodiments, the chamber 160 is positioned between the lens 120 and the sensor 111. The chamber can be in fluid communication with the inlet 170 and the lens 120. The chamber 160 can be substantially water-tight, except for the inlet 170 and the water-permeable lens 120. The chamber can further be in fluid communication with at least one additional reservoir of fluid within the sensor, for example an additional reservoir positioned between the water-tight casing 110 and the inlet 170. The lens 120 can form a surface and/or boundary of the chamber 160. In some embodiments, the fluid-impermeable surface 115 abutting the sensor can form a surface and/or boundary of the chamber. In some embodiments, the chamber has a volume of at least about 0.1 ml. There need be no specific volume range for some embodiments. For laparoscopes, the volume can be very small, such as a few cubic millimeters. A volume that is adequate to distribute fluid across a lens (on the sensor side) can be adequate.

In some embodiments, the chamber is defined by a discrete surface that can be separate from the lens 120 and/or the fluid-impermeable surface 115. In some embodiments, at least a part of the surface of the chamber is the lens 120 and/or the fluid-impermeable surface 115 (as shown in FIG. 1).

In some embodiments of FIG. 1, the fluid-impermeable surface 115 abutting the sensor can be continuous with the watertight casing 110 surrounding the sensor. The fluid-impermeable surface can be affixed to the fluid-tight casing via a seal or attachment such as an adhesive, a tape, a gasket, and/or a weld. The fluid-impermeable surface 115 abutting the sensor can include a sensing surface. The fluid-impermeable surface 115 abutting the sensor can be permeable to what is being sensed, for example electromagnetic radiation, thus permitting what is being sensed to enter the sensor and reach an internal sensing surface 101.

If the fluid-impermeable surface 115 is external to the sensing surface, the electromagnetic radiation can pass through the fluid-impermeable surface. The electromagnetic radiation can include electromagnetic radiation to which the lens 120 is transparent, as described herein. In some embodiments, when the chamber is substantially filled with fluid, at least about 1% of the electromagnetic radiation is transmitted from the lens to the sensing surface of the sensor. Similarly, the fluid-impermeable surface can also be adequately transparent for other signals as well, such as sound, as appropriate.

In some embodiments, the chamber 160 is positioned between the lens 120 and a surface in optical communication with the sensor. In these embodiments, the sensor 111 is optionally positioned between the first end and second end of the sensor device 100. Alternatively, the sensor can be positioned outside of the sensor device and senses electromagnetic radiation that passes through the lens 120 via a surface with which the sensor is in optical communication. For example, in some embodiments, the sensor can be in optical communication via a fiber optic cable, a mirror, a prism, an optical relay device, or a combination thereof, and thus, need not be near and/or within a casing or the chamber 160.

In some embodiments, fluid passes through a filter prior to entering the chamber. The diameter of the largest pore can be at least about 10% larger than the diameter of the largest particle that passes through the filter.

In some embodiments of FIG. 1, the sensor device includes an inlet 170 in fluid communication with a source of fluid 175. The inlet 170 can also be in fluid communication with the chamber 160. The inlet can be connected to a channel, for example a tube or a pipe, or directly to a source of fluid 175, from which fluid flows into the sensor device 100 and into the chamber 160. The inlet can be positioned at the first end 140, the second end 150, or between the first end 140 and the second end 150. The inlet can be positioned so as not to interfere with the path of light passing through the lens into the chamber, which can be a consideration, for example, if the inlet is positioned at or near the second end. The inlet can include a valve. The inlet can include a nipple. The sensor can include two or more inlets.

The source of fluid 175 can include a liquid that was previously being monitored (e.g., 240) but that has been cleaned and/or purified to some extent, for example cleaned water. In some embodiments, the source of fluid 175 includes clean fluid from a main supply, for example clean water from a water main. Various possible fluids are discussed in more detail below.

In some embodiments of FIG. 1, the fluid-impermeable casing 110 is substantially impermeable to a fluid 130. The fluid can include water. The fluid can be in the chamber 160, and/or in a space outside of the watertight casing 110. In some embodiments, a first portion of the fluid-impermeable casing 110 is substantially impermeably to fluid, while a second portion is substantially permeable to fluid, and the second portion is positioned so that it does not contact the fluid. For example, the second portion can extend outside of the first end 140 of the sensor device and be sealed-off by a seal 180, thus preventing the second portion from contacting fluid.

In some embodiments, the chamber contains a fluid. The chamber 160 can be substantially filled with fluid 130. Other spaces outside of the casing 110 can be also be filled with fluid. In some embodiments, a pump 177 moves fluid from a fluid source 175 thorough an inlet 170, and into the chamber 160. The sensor device can include two or more pumps. For example, if the chamber has two or more inlets, the second inlet can be in fluid communication with a second pump. Two or more pumps 177 (second pump not shown) can move fluid into a single inlet 170, and function redundantly in case one pump fails.

In some embodiments, the fluid can include water. The fluid can include substantially pure water. The water can be at least 50% pure by percentage mass of water. In some embodiments, the water is purified waste water. In some embodiments, the water is purified sewage water. The water can be distilled water. The fluid can include an alcohol, for example methanol, ethanol, n-propanol, isopropanol, n-butanol, 2-butanol, or tert-butanol. The fluid can include particles, provided that they do not interfere with the lens 120. The fluid can include a detergent, for example sodium dodecyl sulfate, or a biocide. In some embodiments, the fluid includes a gas. This can be especially useful with the material in the channel 210 includes a gas.

In some embodiments, the pump is one of a positive displacement pump, for example a rotary pump, reciprocating pump, or linear pump; a dynamic pump, for example a centrifugal pump or an axial flow pump; or an impulse pump, for example a hydraulic ram pump or an airlift pump. The flow can also be a gravity fed flow.

In some embodiments, when the fluid passes through the lens 120 it creates an effective fluid boundary of fluid 260 between the lens and the liquid to be monitored. The fluid boundary is on an outer surface of the lens, (which is a surface proximal to the liquid to be monitored), and distal to the sensor. The fluid boundary is such that the outer surface of the lens is not soiled as much by accumulated deposits or contaminants from the liquid (or other material) to be monitored that would otherwise interfere with the monitoring of this liquid (or other material). The fluid boundary can be configured such that the surface of the lens is not soiled as much, but that the fluid boundary does not prevent the sensing of the liquid to be monitored. In some embodiments, the amount of fluid in the fluid boundary and/or the size of the fluid boundary does not prevent the sensor from effectively monitoring the liquid (or other material) in the channel 210. In some embodiments, liquid at least a minimal distance from the surface of the lens has a composition substantially representative of the liquid being sensed.

In some embodiments of FIG. 1, electromagnetic radiation 190 is transmitted through the lens 120, through the chamber 160, and through the fluid-impermeable surface 115 abutting the sensor. Thus, in some embodiments all of these are adequately transparent to electromagnetic radiation.

In some embodiments, the electromagnetic radiation is ambient electromagnetic radiation that can naturally be present in the channel, for example, if the channel has an open top that is exposed to the sky. The electromagnetic radiation can be emitted from a source of electromagnetic radiation positioned so that there is liquid (or other fluid) to be monitored positioned between the source of electromagnetic radiation and the sensor device 100. The electromagnetic radiation can be emitted by the sensor device (or proximally to the sensor device) into the liquid to be monitored, and reflected and/or refracted back to the sensor device. The electromagnetic radiation can be reflected or refracted by a structure, for example a mirror or a prism, positioned so that there is liquid to be sensed between the structure and the sensor device 100.

In some embodiments of FIG. 1, the electromagnetic radiation 190 is transmitted through the lens 120, and through the chamber, and to a surface in optical communication with the sensing surface 101, but not within the sensor device 100.

In some embodiments, the electromagnetic radiation is substantially of a uniform wavelength. In some embodiments, the electromagnetic radiation includes radiation of two or more wavelengths, a range of wavelengths, or two or more ranges of wavelengths. The wavelengths can be wavelengths transmitted by the lens, as described herein. In some embodiments, the wavelength of the electromagnetic radiation is at least about 200 nanometers. In some embodiments, the light includes an IR wavelength, a visible wavelength, an x-ray wavelength, and/or an UV wavelength of radiation.

In some embodiments, the sensor is in data communication with a processor. In some embodiments, of FIG. 1, the sensor is connected to the processor via an electrical and/or optical feed 185. The sensor can be in wireless data communication with the processor. The processor can include and/or be part of a general purpose computer programmed to perform at least one specific function. The processor includes a special purpose computer that performs at least one specific function for detecting and/or recording information regarding the liquid and/or material in the channel 210. The specific function can further include instructing the sensor, for example to detect a signal, to stop detecting a signal, and/or to emit electromagnetic radiation. The specific function can further include instructing the pump to increase the rate of pumping, decrease the rate of pumping, start pumping, and/or stop pumping. The programming can be provided on a computer-readable medium.

In some embodiments, a method of cleaning a sensing device is provided. The method includes providing a sensor surface, providing a fluid-permeable lens, and providing a fluid between the sensor and the fluid-permeable lens. The fluid is allowed to pass through the fluid-permeable lens, thus creating a fluid boundary on an outer surface of the lens to clean the outer surface of the lens. In some embodiments, the pass or flow rate of the fluid through the lens 120 is adequate to reduce contaminant build up on the lens. In some embodiments, the pass or flow rate is adequate to remove and/or reduce at least 50% of the contaminants from the lens. In some embodiments, the pass or flow rate are adequate to build up a barrier of the fluid immediately in front of the lens.

Figure 3:
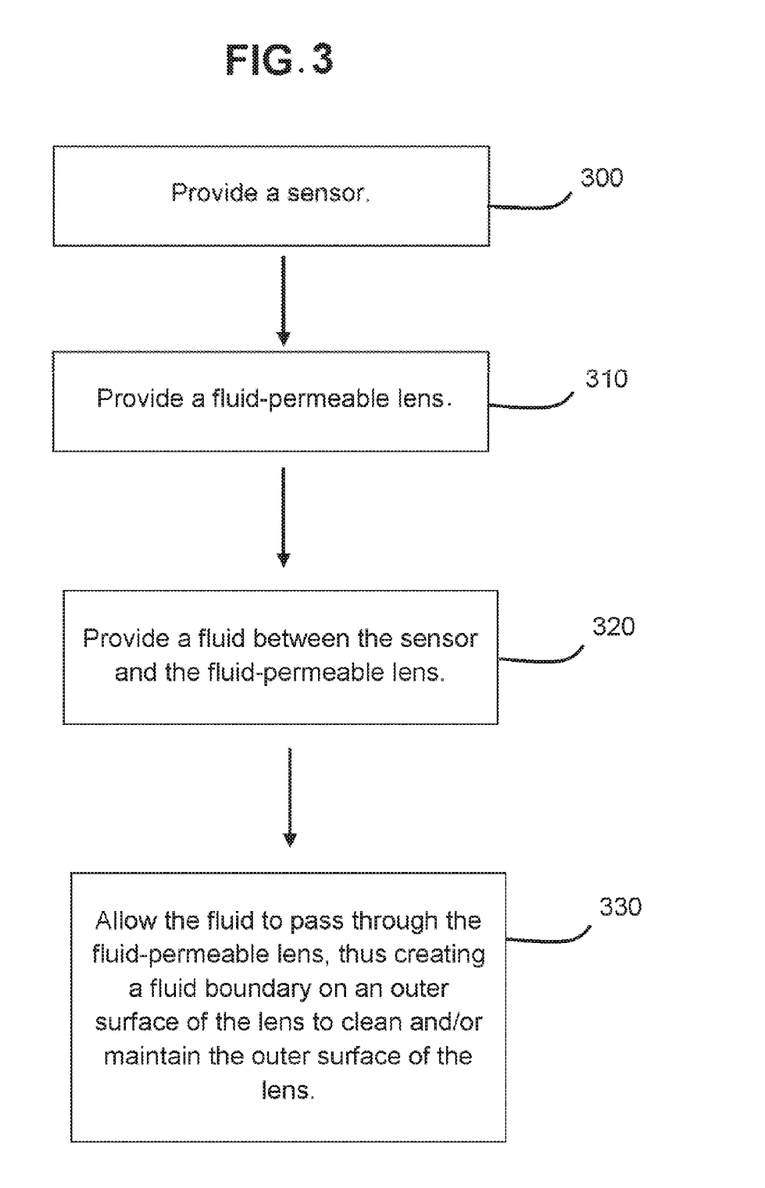
FIG. 3 is a flow diagram illustrating embodiments of a method of cleaning a sensing device.

FIG. 3 is a flow diagram illustrating some embodiments of a method involving the sensing device. A sensor is provided 300, a fluid-permeable lens is provided 310, and a fluid is provided between the sensor and the fluid-permeable lens 320. The fluid passes through the fluid-permeable lens 330. The passage of the fluid through the lens creates a fluid boundary on an outer surface of the lens to clean and/or maintain the outer surface of the lens. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, the method includes providing a sensor, providing a fluid-permeable lens, providing a fluid between the sensor and the fluid-permeable lens, and allowing the fluid to pass through the lens. The fluid passes through the lens at a rate that is adequate to create a fluid boundary on an outer surface of the lens as described herein.

The method can include contacting a surface of the lens with a liquid to be monitored. The liquid to be monitored can be a contaminated liquid. Thus, the surface of the lens can be contacted by contaminated liquid. In some embodiments, the contaminated liquid can be greywater. In some embodiment, the greywater is contaminated relative to the fluid 130 that passes through the lens.

The surface of the lens that contacts the liquid to be sensed 240 can be an outer surface, i.e. a surface proximal to the liquid to be sensed, and distal to the sensor. In some embodiments, although the surface of the lens is initially contacted by a liquid to be sensed, the liquid is displaced by a boundary 260. In some embodiments, the method includes cycling (or recycling) contaminated liquid, for example greywater through a cleaning system in fluid communication with the lens 120, thus providing fluid to the lens. Thus, contaminated liquid can be cycled (or recycled) through a cleaning system and serve as a fluid for cleaning the lens, passing through the lens, and ultimately returning to the body of contaminated liquid.

In some embodiments, the fluid is under hydraulic pressure. The fluid can be placed under hydraulic pressure by at least one pump as described herein. In some embodiments the amount of pressure that a fluid is under depends on the pressure restriction of the lens design and the structural strength of the material it is made from. The pressure restriction can help regulate the liquid flow through the lens so it does not have to be much lower. In some embodiments, the liquid being monitored is under hydraulic pressure, and the fluid is under a greater hydraulic pressure. In some embodiments, the fluid can be under a hydraulic pressure that is at least about 105% of the pressure of the liquid being sensed. In some embodiments, the fluid is not under hydraulic pressure, having a pressure substantially the same as that of the liquid being monitored. In some embodiments, the fluid can passively enter the channel 210, for example by diffusion or reverse osmosis, thus cleaning the lens.

In some embodiments, the fluid 130 is at least 1% cleaner than the material in the channel 210 to be examined. In some embodiments, the fluid 130 is not purer or cleaner, as an absolute measurement, than the material to be monitored; however, the fluid can have a lower amount of a contaminant that is likely to build up on the lens 120. Thus, in some embodiments, the fluid need only have a lower amount of contaminants that can build up and/or adhere to the lens 120.

In some embodiments, the fluid includes at least one of water or an alcohol. In some embodiments, the fluid is obtained from and/or stored in an external source, for example a water main or storage tank. In some embodiments, the fluid is from a cleaned or decontaminated liquid derived from the liquid (or other material) being monitored. The fluid can be from an amount of greywater than has been at least partially purified. Thus, the fluid can be an amount of greywater that was previously monitored by the sensor. In some embodiments, when the fluid is from an amount of cleaned liquid derived from the liquid being monitored, when the fluid passes through the lens it is returned to the liquid being monitored, thus permitting multiple cycles of monitoring and cleaning or decontamination.

In some embodiments, the fluid passes through at least one pore in the lens. In some embodiments, the fluid passes through multiple pores. The fluid can contain particles. The diameter of the largest pore can be larger than the diameter of the largest particle or particles, thus permitting the particles to pass through the lens, and preventing buildup of contaminants on an inner surface of the lens.

In some embodiments, the fluid passes through the lens at a constant rate. In some embodiments, the fluid passes through the lens at a variable rate. For example, the fluid can be pulsed through the lens at various time points. In some embodiments, the average rate by which the fluid moves through the lens is at least about 0.1 liter per day. In some embodiments, the average rate by which the fluid moves through the lens is at least about 0.005 liter per square millimeter per day.

In some embodiments, a fluid-permeable lens is provided. The lens can include a fluid-permeable membrane. The membrane further can be transparent to at least one wavelength of electromagnetic radiation. The membrane further can have a refractive index substantially identical to a refractive index of water. The membrane can allow water to passively pass through the lens as described herein. In some embodiments, the lens is water-permeable. In some embodiments, the lens is solvent permeable.

FIG. 4 illustrates some embodiments of lenses. FIG. 4A illustrates a polytetrafluoroethylene lens 300. In some embodiments, the lens includes at least one layer of polytetrafluoroethylene 310. In some embodiments, the lens includes perforations or pores 320 in the polytetrafluoroethylene.

Figure 4A:
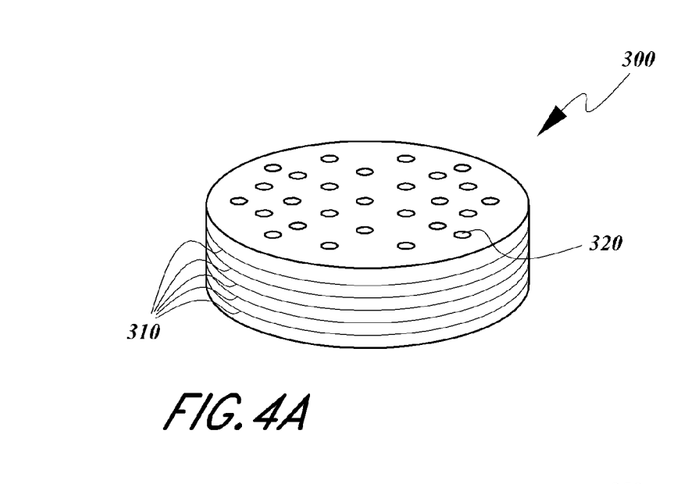
FIG. 4A is a drawing illustrating some embodiments of a lens.
Figure 4B:
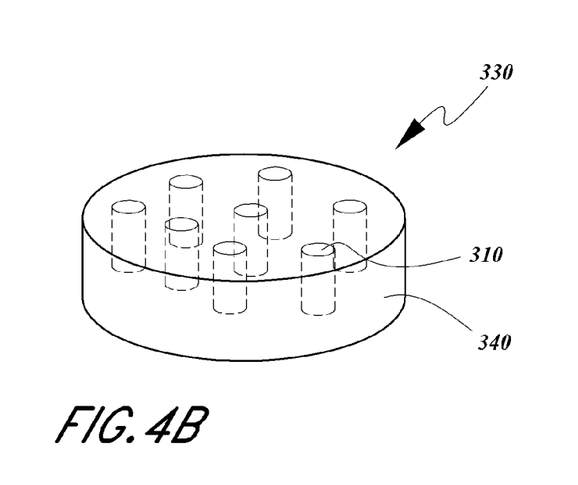
FIG. 4B is a drawing illustrating some embodiments of a lens.

FIG. 4B illustrates some embodiments of a polytetrafluoroethylene lens 330. In some embodiments, the lens includes at least one layer of polytetrafluoroethylene 310. In some embodiments, the lens includes drilled or laser-bored holes 340 in the polytetrafluoroethylene.

Figure 4C:
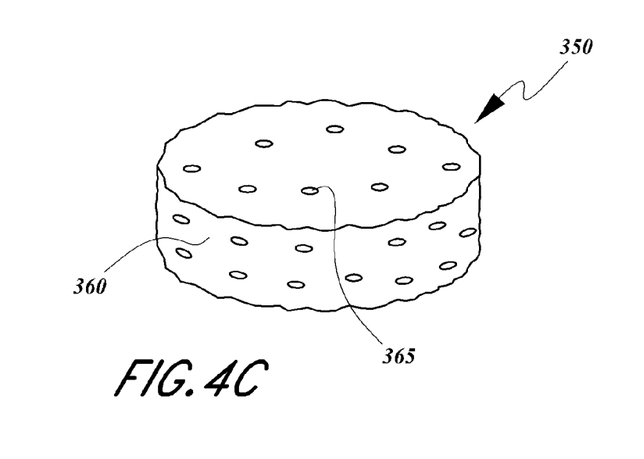
FIG. 4C is a drawing illustrating some embodiments of a lens.

FIG. 4C illustrates some embodiments of a foamed polytetrafluoroethylene lens 350. In some embodiments, the lens includes foamed polytetrafluoroethylene 360 and the foamed polytetrafluoroethylene includes water-permeable porous structures 365.

Figure 4D:
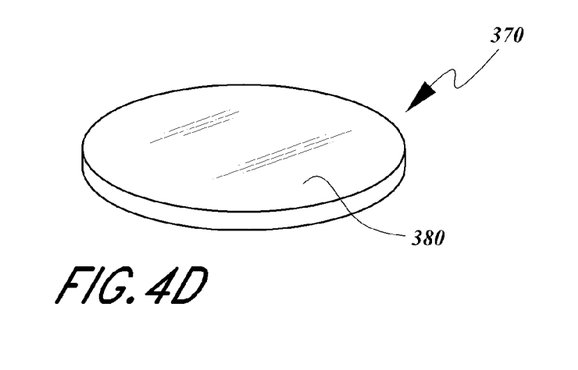
FIG. 4D is a drawing illustrating some embodiments of a lens.

FIG. 4D illustrates some embodiments of a polymer lens 370 that includes transparent forms of at least one polymer 380, for example transparent silicone and/or transparent nylon.

In some embodiments, the membrane allows water to passively pass through the lens at a rate of at least 0.1 liter per day. However, the rate will depend upon the material in the channel, the composition of the fluid, the particular lens, and the degree to which the lens should be kept clean. In some embodiments, the water passes through the lens via diffusion. In some embodiments, the water passes through the lens via reverse osmosis.

In some embodiments a system for monitoring a liquid is provided. In some embodiments, the system includes a system for monitoring a greywater channel. The system can include a sensor device that can include a fluid-permeable lens as described herein.

Figure 5:
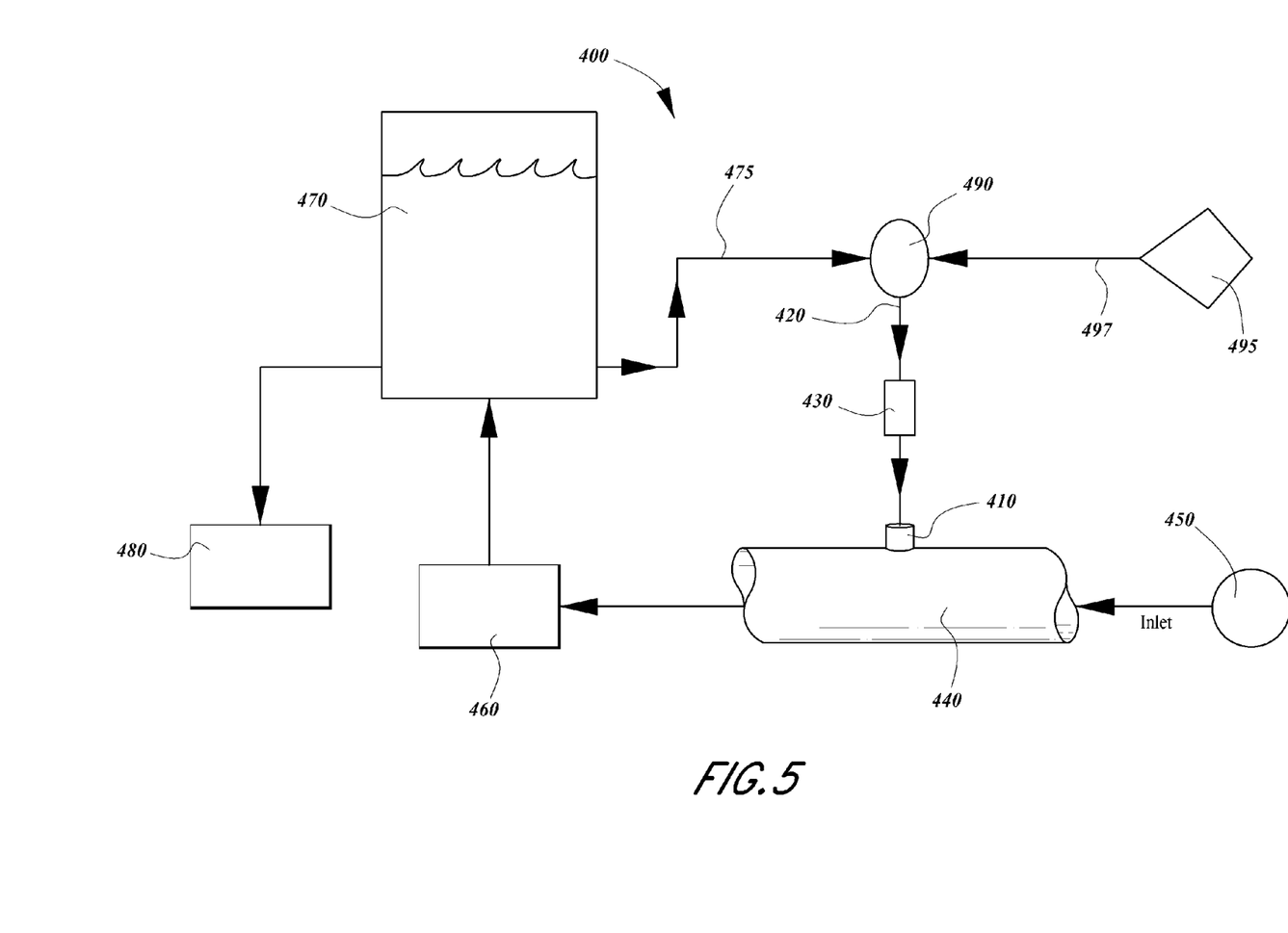
FIG. 5 is a drawing illustrating some embodiments of a greywater monitoring system.

FIG. 5 illustrates some embodiments of a system for monitoring a liquid 400. The system can include a sensor device 410. The system can further include an input channel 420 in fluid communication with the sensor. The system can optionally include a filter 430 in fluid communication with the sensor device 410. The system can further include a sensed-fluid channel 440 for the liquid (or other fluid) to be monitored. The system can further include a source of the liquid (or other fluid) to be monitored 450. The sensed-fluid channel 440, for example a greywater channel, can be in fluid communication with a fluid cleaning system 460. The system can further include a cleaned fluid holding tank 470. The cleaned fluid holding tank can be in fluid communication with an end use outlet 480. The fluid cleaning system 460 can be in fluid communication with the cleaned fluid holding tank 470. The cleaned fluid holding tank 470 can be in fluid communication with an optional cleaned-fluid channel 475 that is in fluid communication with the sensor device 410. The cleaned-fluid channel 475 can be in fluid communication with an optional control valve 490, which is in fluid communication with the input channel 420. A main fluid supply 495 can optionally be in fluid communication with the control valve 490. A channel 497 can connect the main fluid supply 495 to the control valve 490.

In some embodiments, the system includes an optical sensor device as described herein. The system can further include a fluid permeable lens as described herein. The system can further include a source of cleaning fluid in fluid communication with the fluid-permeable lens.

In some embodiments, the source of the fluid for cleaning the lens includes a main fluid supply and/or cleaned fluid obtained from the liquid to be monitored. The system can include a main fluid supply 495, which can be, for example, a water main. The system can include a cleaned fluid holding tank 470 for fluid obtained from the liquid to be monitored, for example, cleaned water obtained from greywater as described herein. If the system includes both a cleaned fluid holding tank 470 and a main fluid supply 495, the control valve can direct the flow of fluid from neither, one, or both sources. For example, if the cleaned fluid tank 470 is substantially depleted, the control valve 490 can shut-off the flow of fluid from the cleaned fluid tank 470, and instead direct the flow of fluid from the main fluid supply 495. In some embodiments, the system further includes a processor in data communication with the control valve. The processor can be programmed to open or shut the control valve to direct the flow of fluid from the cleaned fluid tank, the main fluid supply, both sources, or neither source. The selection of source can depend on availability of fluid, requirements for fluid, or other considerations.

In some embodiments, the source of cleaning fluid is in fluid communication with the fluid permeable lens. In some embodiments of FIG. 5, the source of cleaning fluid 470 is in fluid communication with a cleaned fluid channel 475. The cleaned fluid channel can be in fluid communication with a control valve 490. Alternatively, the cleaned fluid channel 475 can bypass the control valve and connect directly to a filter or the sensor. Alternatively, the cleaned fluid tank 470 can contact the control valve or the filter or the sensor without the use of the cleaned fluid channel. In some embodiments, two or more cleaned fluid channels provide parallel or alternate paths of fluid delivery.

In some embodiments, the primary fluid supply includes a water main. In some embodiments, the primary fluid supply includes a storage tank to which fresh or clean fluid is added. In some embodiments, the cleaned fluid holding tank has a fixed capacity. In some embodiments, the cleaned fluid holding tank is one of a bag, a bladder, a canister, a jug, a bucket, a cylinder, a hopper, a capsule, or a cylinder. In some embodiments, the cleaned fluid tank has a capacity of at least 0.1 liters.

In some embodiments, the sensed-fluid channel 440 includes at least one of a pipe, a tunnel, a groove, a ditch, a canal, a reservoir, a tube, a conduit, a waterfall, or a pool. In some embodiments, liquid in the channel is not a flowing liquid. In some embodiments, the liquid in the channel is moving. The liquid in the channel can be moving at a rate of at least about 0.1 liters per minute.

In some embodiments, the system includes an inline filter. The filter can be in fluid communication with the fluid-permeable lens. In some embodiments of FIG. 5, the filter 430 can be optionally positioned between the control valve 490 and the sensor device 410. In some embodiments, the filter 430 can be positioned between the main fluid supply 495 and the sensor device 410, or between the cleaned water tank 470 and the sensor. In some embodiments, the filter 430 can be positioned between the cleaned water tank 470 and the control valve 490, or between the main fluid supply 495 and the control valve 490.

In some embodiments, the filter is a mesh filter, Millipore filter, nanopore filter, carbon filter, diatomaceous earth filter, and/or reverse osmosis filter.

In some embodiments, the system includes two or more filters. Two or more filters can be positioned serially. A first filter can be positioned in a first portion of the system, for example between the cleaned fluid holding tank and the control valve, and a second filter can be positioned in a second portion of the system, for example between the main fluid supply and the control valve.

In some embodiments, the filter permits the passage of particles with diameters that are smaller than the diameter of the largest pore of the fluid-permeable lens. In some embodiments, the largest particles permitted to pass through the filter have a diameter at least about 5% smaller than the diameter of the largest pore of the fluid-permeable lens. In some embodiments, the filter permits the passage of a particle having a diameter no greater than about 195 µm. In some embodiments, the filter permits approximately 0.3 nephelometric turbidity units (NTU).

Some embodiments provide a self-cleaning lens for optical sensors used in greywater treatment systems, where sensors tend to foul quickly.

In some embodiments, a device is provided, including an optical sensor that is encapsulated in a watertight shell, and then encased in a small chamber adapted to receive clean water from a clean water source. The lens itself forms the front-of-sensor part of the outer casing holding the clean water. The material of the lens itself is transparent, permeable, and has the same refractive index as water. Under hydraulic pressure, clean water passes through the lens, and out into the greywater. As water passes through the lens it creates a clean water boundary layer that keeps the outside surface of the lens clean.

The lens can be constantly submerged in greywater.

The amount of clean water used can be a few liters or less per day, and is recycled back into the greywater treatment system.

Some embodiments include adaptations for non-optical sensors, such as transducers, and have applications beyond the scope of greywater environments.

Some embodiments provide a self-cleaning lens for optical sensors in greywater systems. The sensor can be used, for example, for sensing turbidity of the greywater.

The lens can include a material that is transparent, permeable and has the same refractive index as water, but it is not possible to get a material with all three features.

FIG. 2 depicts some embodiments of the installation of the sensor and lens in a greywater pipe. Ideally, the sensor device is located in the vicinity of the 3 o'clock or 9 o'clock positions and not bottom dead center (to prevent any solids build up with gravity). To prevent the fluid boundary layer being disturbed by the main flow of the greywater, the sensor is recessed beyond the diameter of the pipe, reducing recirculation in the recess. Baffles are another option to overcome this.

Some embodiments include an impinging spray or jet of clean water hitting the lens (which then need not be fluid permeable) and/or jets of water or other fluid surrounding the lens. In some embodiments, a permeable zone is provided around the lens so as to provide the fluid boundary proximal to the lens. In some embodiments, the zone is a ring around, or substantially around, the lens. In such embodiments, the lens itself need not be permeable.

Some embodiments provide devices that can be used in conjunction with other applications, for example laparoscopes when fouling the viewer is an issue.

EXAMPLE 1

Sensor Device

An optical sensor is encased in a plastic, water-tight casing. The casing is positioned at the second end of a sensor device.

A water permeable lens is provided. The lens includes 5 layers of polytetrafluoroethylene film, each layer having an average thickness of about 0.1 mm. The 5 layers are stacked on top of each other, and annealed thermally. The lens has pores covering about 5% of its surface area. The diameters of the pores range from about 0.005 millimeters to about 0.05 millimeters. Thus, the pores permit the passage of fluid and particles having diameters of less than about 0.05 millimeters through the lens. The lens has a refractive index of about 1.4. The lens is about 95% transparent to electromagnetic radiation having a wavelength of about 400 nm.

The lens is positioned flush with a first end of the sensor device. The optical sensor is positioned flush with the second end of the sensor device. A chamber having a volume of about 20 milliliters is positioned between the sensor and the lens. A polytetrafluoroethylene surface is positioned between the optical sensor and the chamber, and abuts the water-tight-casing surrounding the sensor. The chamber is in fluid communication with an inlet positioned near the second end of the chamber, connected to the inlet by a cavity between an outer surface of the chamber and the water-tight casing surrounding the sensor. A rotary pump pumps clean fluid from a clean fluid holding tank into the inlet, and thus into the chamber at a rate of about 0.5 liters per day. The fluid is made of 99% pure water by mass. The fluid passes through the chamber, and flows through the lens, thus forming a boundary layer of clean water extending about 0.5 mm beyond the outer surface of the lens, thus keeping the lens clean.

A radiation source on a side of a channel of greywater being monitored opposite the sensor device emits electromagnetic radiation having a wavelength of about 400 nm. The electromagnetic radiation passes through the greywater, is transmitted by the lens, is transmitted through fluid in the chamber, and is transmitted through the polytetrafluoroethylene surface to arrive at a sensing surface of the sensor. The sensor, via the sensing surface, senses the intensity and wavelength of the electromagnetic radiation. A USB cable extending out of the second end of the sensor connects the sensor to a processor. The processor includes a general purpose computer that is programmed to store data collected by the sensor at ten-second intervals. A rubber O-ring seal seals the space between the sensor and the second end of the chamber, thus preventing fluid from leaking out the second end. Thus, a sensor device is provided and can monitor the purity of greywater, while maintaining a relatively clean protective lens with the use of no more than water as a cleaning tool.

EXAMPLE 2

Fluid Permeable Lens

The lens includes a single layer of permeable silicone. The layer is about 2 mm thick. The lens is substantially circular and has a diameter of about 5 cm. The lens has a refractive index of about 1.3. The lens is about 98% transparent to electromagnetic radiation having a wavelength of about 580 nm. The lens permits about 100 ml of water to pass through the lens each day when the water is applied at 1 Pa.

EXAMPLE 3

System for Monitoring Greywater

Provided herein is an example of a system for monitoring greywater. The system includes a sensor device positioned in a recessed space off of a pipe for greywater. The sensor device includes a fluid permeable lens made of foamed polytetrafluoroethylene. The lens is substantially oval-shaped, is about 2 mm thick, has a surface area of about 10 cm$^2$, and has a refractive index of about 1.35. The lens includes pores having an average diameter of about 0.05 mm, but ranging in diameter from 0.01 mm to 0.07 mm covering about 3% of its surface area. The lens is about 98% transparent to electromagnetic radiation having a wavelength of about 750 nm.

The sensor device includes an optical sensor. The optical sensor is positioned outside of the recessed space, and about 5 meters away. The optical sensor itself is not waterproof. The sensor device includes a fiber optic cable connecting a sensing surface of the optical sensor to a surface positioned 1 mm from an inner surface of the lens. Thus, there is a chamber of a volume of about 0.5 ml between the lens and the surface connected to the fiber optic cable. The fiber optic cable passes through the second end of the sensor, and is surrounded by a silicone gasket, so that the second end of the sensor device remains substantially watertight.

Greywater flows through the pipe at a rate of about 1000 liters per hour. A greywater cleaning system cleans about 1000 liters of water per hour via reverse osmosis filtration, producing 97% pure water by mass, and depositing that cleaned water in a cleaned water holding tank. The cleaned water holding tank is in fluid communication with an irrigation system for a garden (i.e. an end use outlet). The cleaned water holding tank is connected via a pipe to a control valve, which is controlled by a processor programmed to permit the flow of cleaned water so long as the cleaned water holding tank contains at least 1 liter of water. The cleaned water passes through the control valve, through a pipe, to a reverse osmosis membrane filter that only permits the passage of particles having a diameter smaller than about 200 micrometers. The filtered water is pumped into the sensor device via a displacement pump at a rate of about 0.5 liters per day. The water enters the chamber between the lens and the surface in optical communication with the sensor, and passes through the lens (entering the inner surfaced, and exiting the outer surface) via reverse osmosis at a rate of about 0.5 liters per day. The water forms a fluid boundary layer extending about 5 millimeters over the surface of the lens, thus reducing contaminants from contacting the lens.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A sensor device comprising:
    a sensor comprising a sensing surface;
    a cylindrical housing within which the sensing surface is positioned, the cylindrical housing including a cylindrical wall and a disc-shaped end wall at a first end of the cylindrical wall;
    a transparent, liquid-permeable lens included in the disc-shaped end wall and positioned in front of the sensor; and
    an enclosed chamber positioned between the sensor and the transparent, liquid-permeable lens, such that radiation can pass through the transparent, liquid-permeable lens and into the sensor to the sensing surface,
    wherein the transparent, liquid permeable lens forms at least one surface of the enclosed chamber, wherein the transparent liquid-permeable lens contains openings of less than 100 micron diameter through which a liquid can pass, and wherein the enclosed chamber is in fluid communication with an inlet, so that when the liquid is applied under hydraulic pressure into the enclosed chamber through the inlet, the liquid is forced through the openings in the transparent, liquid-permeable lens at a level sufficient to clean the transparent, liquid-permeable lens.

2. The sensor device of claim 1, wherein the sensor is an optical sensor.

3. The sensor device of claim 1, wherein the sensor is a laparoscopic sensor.

4. The sensor device of claim 1, wherein the sensor is a transducer.

5. The sensor device of claim 1, wherein the transparent, liquid-permeable lens has a refractive index that is similar to water.

6. The sensor device of claim 1 wherein the transparent, liquid-permeable lens is positioned at a first end of the chamber, and the sensor is positioned at an opposite end of the chamber.

7. The sensor device of claim 1, wherein the sensor is substantially impermeable to a fluid.

8. The sensor device of claim 1, wherein at least one surface of the chamber is formed by a surface abutting the sensor.

9. The sensor device of claim 8, wherein the surface abutting the sensor is water impermeable.

10. The sensor device of claim 1, further comprising a source of electromagnetic radiation.

11. The sensor device of claim 1, wherein the sensor is in electrical communication with a processor.

12. The sensor device of claim 1, further comprising the liquid disposed in the enclosed chamber and permeating the transparent, liquid-permeable lens, wherein the liquid comprises a cleansing liquid.

13. The sensor device of claim 12, further comprising a buffer layer of cleansing liquid positioned on an exterior surface of the transparent, liquid-permeable lens that is also an exterior surface of the sensor device, wherein the buffer layer of cleansing liquid is positioned between the exterior surface of the transparent, liquid-permeable lens and a contaminated liquid.

14. The sensor device of claim 1, wherein the enclosed chamber is water-tight except for an inlet in fluid communication with a liquid source and the transparent, liquid-permeable lens as an outlet.

15. The sensor device of claim 1, wherein the transparent, liquid-permeable lens comprises a plurality of layers of polytetrafluoroethylene film.

16. The sensor device of claim 1, wherein the transparent, liquid-permeable lens comprises silicone.

\* \* \* \* \*